Figure 1:
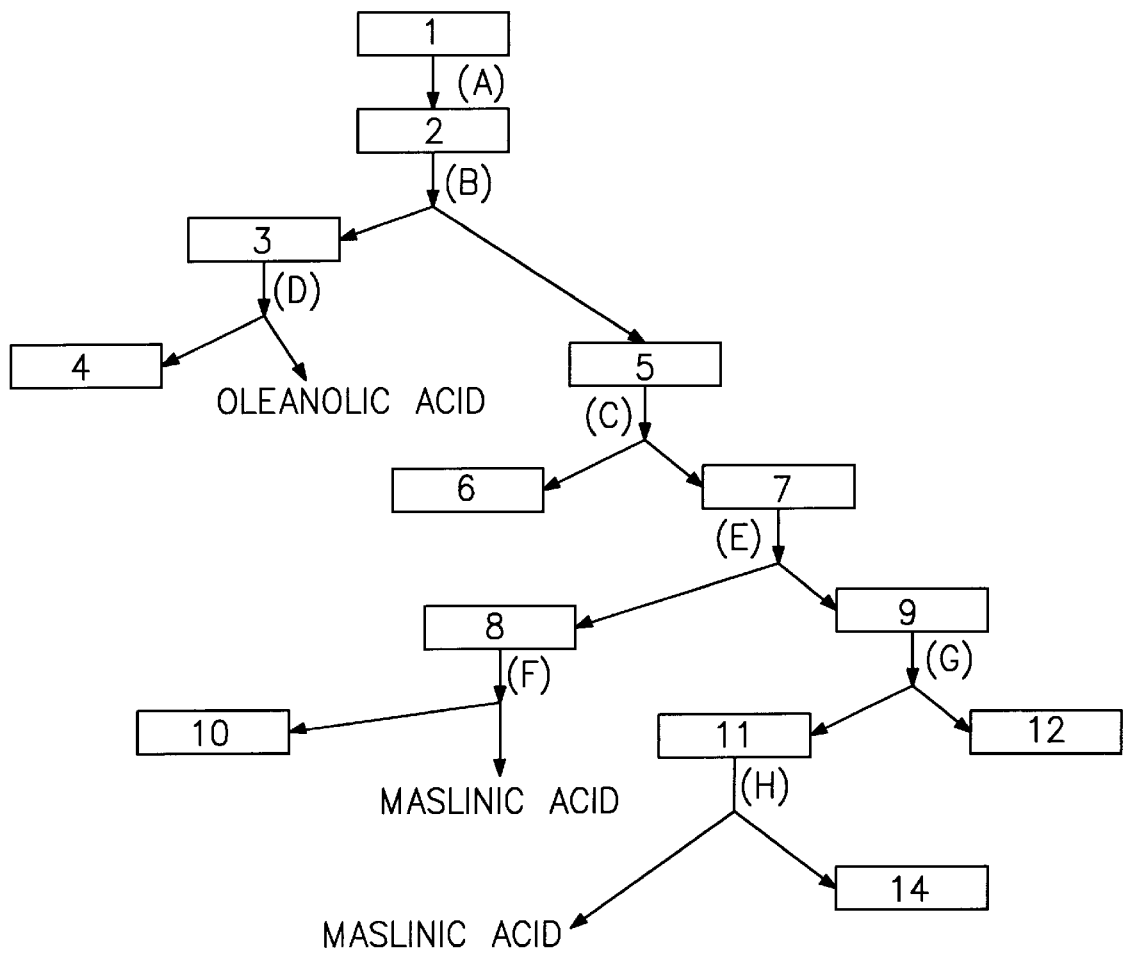

United States Patent [19]
Lopez de Hierro

[11] Patent Number: 6,037,492
[45] Date of Patent: Mar. 14, 2000

[54] PROCESS FOR THE INDUSTRIAL RECOVERY OF OLEANOLIC AND MASLINIC ACIDS CONTAINED IN THE OLIVE MILLING SUBPRODUCTS

[75] Inventor: Andrés Garcia-Granados Lopez de Hierro, Granada, Spain

[73] Assignee: Universidad de Granada, Granada, Spain

[21] Appl. No.: 09/043,318

[22] PCT Filed: Jul. 24, 1997

[86] PCT No.: PCT/ES97/00190

§ 371 Date: Mar. 20, 1998

§ 102(e) Date: Mar. 20, 1998

[87] PCT Pub. No.: WO98/04331

PCT Pub. Date: Feb. 5, 1998

[30] Foreign Application Priority Data

Jul. 25, 1996 [ES] Spain ...................................... 9601652

[51] Int. Cl.[7] .................................................... C07C 61/12
[52] U.S. Cl. ............................................................ 562/498
[58] Field of Search ............................................... 562/498

[56] References Cited

PUBLICATIONS

Database CAPLUS on STN, Acc. No. 1986:423292, Lanzani et al., 'Olive marc: transformation and recovery technology of by–products for practical appliacations. Note I.' Riv. Ital. Sostanze Grasse (1985), 62(11), pp. 597–604, abstract.

*Primary Examiner*—Gary Geist
*Assistant Examiner*—Brian J. Davis
*Attorney, Agent, or Firm*—Lackenbach Siegel Marzulla Aronson & Greenspan

[57] ABSTRACT

Process for the recovery of oleanolic and maslinic acids contained in the subproducts resulting from the milling and processing of olives or parts thereof, either proceeding from three-phase or two-phase presses. This process enables to obtain, by separation and with purities higher than 80%, of both acids with yields comprised between 0.2 and 1.5%, as a function of the product and prime material processed. Fundamentally, it comprises selective extractions and fractionation of resulting mixtures with the use of solvents.

10 Claims, 1 Drawing Sheet

PROCESS FOR THE INDUSTRIAL RECOVERY OF OLEANOLIC AND MASLINIC ACIDS CONTAINED IN THE OLIVE MILLING SUBPRODUCTS

This application is a 371 of PCT/ES97/00190 filed Jul. 24, 1997.

PRIOR ART

The cultivation of olive trees is very important in temperate countries almost throughout the world. The trees are primarily used for olive oil, and Spain is currently a producer of over a million metric tons. Classic olive milling and oil production processes consist of the so-called both continuous and discontinuous "three-phase" processes. In addition to oil, these processes yield such by-products as oil-foot, an aqueous fraction of olives with or without the addition of water, and the various types of pressed olive refuse, which is generally extracted for an additional recovery of oil. In addition to three-phase processes, a so-called "two-phase" process is used which, in addition to oil, yields a mass containing the pulp remains and usually, although not always, the olive stone, mixed with the plant water, resulting in a by-product which is beginning to be known as the "oil-foot refuse".

Oleanolic (3-betahydroxy-28-carboxyoleanene) acid is a triterpenic acid ubiquitously distributed within the plant kingdom. The United States Department of Agriculture phytochemical database (Internet address http://probe.nalusda.gov: 8300/cgi-bin/browse/phytochemdb) has indeed noted its presence in almost a hundred plants, inter alia the *Olea europaea,* and moreover a number of proven biological activities (abortifacient, anticariogenic, antifertility, antihepatotoxic, anti-inflammatory, antisarcomic, cancer-preventive, cardiotonic, diuretic, hepatoprotective and uterotonic). Publications are continuously being made regarding the potential biological activity of this acid and its glycosides. It has indeed been studied for activity as an inhibitor of the proliferation of leukaemia cells (Essady, D., Najid, A., Simo, A., Denizot, Y., Chulia, A. J., and Delage, C.; *Mediators of Inflammation* (1994) 3, 181–184), a hypoglucemiant (Yoshikawa, M., Matsuda, H., Harada, E., Mukarami, T., Wariishi, N., Marakami, N. and Yamahara, J., *Chemical & Pharmaceutical Bulletin* (1994) 42, 1354–1356) an antitumoral (Ohigashi, H., Mukarami, A. and Koshinizu, K. ACS *Symposium Series* (1994) 547, 251–261), a producer of antagonist effects in anaphylactic shock (Zhang, L. R. and Ma, T. X.; *Acta Pharmacológica Sinica* (1995) 16, 527–530), a hepatoprotector (Liu, Y. P., Parkinson, A. and Klaasen, C. D.; *Journal of Pharmacology and Experimental Therapeutics* (1995) 275, 768–774; Connolly, J. D. and Hill, R. A. *Natural Product Reports* 12, 609–638 (1995), and an anti-inflammatory (Recio, M. D., Giner, R. M., Manez, S. And Rios, J. L., *Planta Medica* (1995) 61, 182–185. A specific review of the pharmacological activity of oleanolic acid has been published (Liu. J. *Journal of Ethnopharmacology* (1995) 49, 57–68). Maslinic (2-alpha,3-betadihidroxy-28-carboxyoleanene) acid, also known as crataegolic acid, is far less widespread in nature, and has been found in a dozen plants (Internet Address http://probe.nalusda.ov: 8300/cgi-bin/browse/phytochemdb). It is known (Internet Address http://probe.nalusda.gov:8300/cgi-bin/browse/phytochemdb) to have antihistaminic and anti-inflammatory activity although it has not been extensively studied because of its scarcity. The isolation of oleanolic and maslinic acids from waxes on the surface of the fruit of the *Olea europaea* has been described (Bianchi, G., Pozzi, N. And Vlahov, G. *Phytochemistry* (1994) 37, 205–207) by means the methanol extraction from olives previously washed with chloroform. The separation of aids of this type has been described by means of high-speed counter-current chromatography (HSCCC) (Du, Q. Z., Xiong, X. P. and Ito, Y.; *Journal of Liquid Chromatography* (1995) 18, 1997–2004).

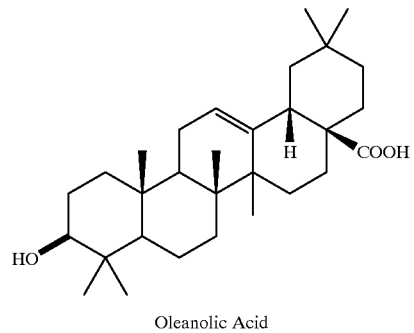

Oleanolic Acid

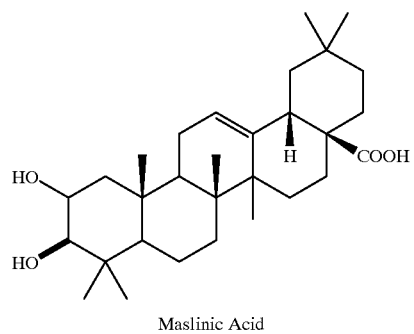

Maslinic Acid

DESCRIPTION OF THE INVENTION

Oil cakes, obtained by classic pressing, "three-phase" processing pressed olive refuse, oil-foot refuse obtained from the so-called "two-phase" system and broadly speaking any residue from the processing of whole olives or parts thereof containing their original skin residues, with or without subsequent processing to recover the oil they contain, with or without preliminary washing, suitably dried until a suitable extent of humidity is attained for their extraction with hexane (or any other solvent or solvent mixture) in the usual manner of pressed olive refuse processing industries, are extracted with an apolar solvent (preferably hexane) to obtain the well-known pressed olive refuse oil after the solvent is eliminated. The oil thus obtained, or diluted with hexane, is left to rest and a white precipitate appears which may be separated from this oil by filtration and/or centrifugation, yielding a semisolid product that after being suitably washed with an apolar solvent (preferably hexane) yields oleanolic acid, which may undergo bleaching processes as desired. The "pressed olive refuse" already extracted as described hereinbefore will be newly extracted with a more polar solvent, preferably ethyl acetate, including liquefied gases under "supercritical" conditions. The volume of the subject extract will be reduced by eliminating the solvent, preferably bringing it to dryness. The extract thus obtained will be treated with a solvent more polar than ethyl acetate, preferably methanol, or with liquefied gases under "supercritical" conditions, yielding a solution and a viscous precipitate that will be separated from the solution by centrifugation and/or filtration. This process may be repeated to increase the quantity of maslinic acid resulting from this operation, as noted below. This insolubilised product in methanol or the liquefied gases will then be washed with an apolar solvent, preferably hexane, and preferably with heating, yielding an undissolved solid which is maslinic acid. An inverse polarity treatment may on the contrary be carried out, in which case the solubilised product would be primarily maslinic acid. The above-mentioned ethyl acetate polar solution is concentrated, as the case may be, preferably to dryness, and is subjected to a treatment or successive treatments with water at different pH values. After a basic water treatment, a precipitate remains that is separated from the washing waters, namely maslinic acid salt. The subsequent treatment of this salt with acid media, preferably minerals, or with any type of ionic exchange treatment, results in free maslinic acid.

EXPLANATION OF FIGURE 1

Product 1: Industrial material resulting from the milling of olives by any process, containing the olive skin and accompanying materials.

Operation (A): Where appropriate, eliminating the water the product 1 contains down to a water content of less than 15% (Product 2). Rotary furnaces or counter-current drying may inter alia be used. For instance, 350 kg of this product 2 are originally taken.

Operation (B): Hexane extraction of Product 2. This may be continuous or discontinuous. This operation recovers some 21 kg from the original 350 kg (some 6%).

Operation (C): Ethyl acetate extraction of the hexane-insoluble solid (product 5) taken from the above-described operation (B). This may be continuous or discontinuous. This operation recovers approximately a further 24 kg from the original product (some 6.5% with respect to product 2).

Operation (D): Partial concentration of product 3 and separation of the precipitate by filtration and/or centrifugation, or fully concentrating product 3 and subsequently diluting it with hexane, filtering and/or centrifuging the precipitated solid, which will be repeatedly washed with solvents (e.g. hexane). A solution will thus be obtained which, upon the solvent being eliminated, will yield oil (19.5 kg) (product 4) and oleanolic acid (0.07% of product 2), which may undergo bleaching processes.

Operation (E): Concentrating the ethyl acetate extract from operation (C) and washing the resultant solid (24 kg) with methanol (75 kg), separating the resultant solution (product 7) from the insoluble solid (product 8) by filtration and/or centrifugation.

(F): Hot-washing the solid (8) taken from the operation described in (E) with hexane, separating the residual solid (maslinic acid, 0.04 to 0.2% with respect to product 2) from the resultant solutions (10) by filtration and/or centrifugation.

(G) Concentrating the methanol solution taken from operation (E) and washing the resultant solid with water (75 kg), preferably with heating, separating the insoluble part (product 11) from the solution (12) by filtration and/or centrifugation.

(H) Treatment with basified water (75 kg), e.g. with 5% sodium hydroxide, to obtain a solution (14) and a set of scarcely soluble maslinic acid salts which are separated from said solution by filtration and/or centrifugation. The maslinic acid is subsequently released by treating the salts in acid media (0.1 5 to 0.35% with respect to solid 2).

A practical embodiment of the process subject of the present Patent will now be set forth.

EXAMPLE 1,000 kg of oil-foot refuse taken from the milling of olives by the so-called "two-phase" process are originally taken. This oil-foot refuse is then dried in a purposely adapted rotary furnace, eliminating most of the water it contains until a humidity of around 8% is attained, thereby obtaining some 350 kg of a material which may be beneficially used, which is then extracted with hexane in facilities typical of the pressed olive refuse processing industry. The hexane extract contains some 6% by weight of non-volatile material, and largely consists of the so-called pressed olive refuse oil (between 5 and 6%) in a highly variable proportion depending on the quality, nature and "history" of the processed pressed olive refuse. The oil thus obtained (some 21 kg) is diluted with 50 Liters of hexane and left to rest at room temperature until a whitish precipitate appears, which is separated from the solution by centrifugation. The solid thus obtained is successively washed with hexane, the solid being separated in each step from the solution by centrifugation. The resultant solutions are brought to dryness and the residue undergoes new hexane washing operations. The resultant solid is added to the first solid obtained, which altogether provides a yield of close to 0.1% oleanolic acid with a richness of at least 85%, maslinic acid being the main accompanying material (some 10%) together with fatty residues. After dissolving the oleanolic acid in a chloroform/methanol mixture, activated carbon is added, and it is boiled for a few minutes, filtered or centrifuged and brought to dryness, yielding some 350 g (between 0.07 and 0.1% with respect to the dry oil-foot refuse) of white oleanolic acid, with a richness in excess of 85%, verified by nuclear magnetic resonance and chromatography. The solid oil-foot refuse already extracted with hexane, of which some 325 kg remain, undergoes ethyl acetate extraction in the same facilities described for hexane extraction. An ethyl acetate solution is thus obtained which is vacuum concentrated up to a solid material content of some 50% and finally brought to dryness by atomisation, to yield some 24 kg of a solid material which is treated with 150 liters of boiling methanol, allowed to cool at rest and then centrifuged. The solid obtained is hot-washed with hexane, yielding some 150 g of washed solid, which is separated by centrifugation from the hexane solutions. This solid is dissolved in a chloroform/methanol mixture and bleached with activated carbon, thereby for some 130 g (0.04% with respect to the dry processed oil-foot refuse) of a white solid to be obtained, which is maslinic acid with a richness in excess of 85%, accompanied by some 10% oleanolic acid. The materials solubilised in methanol are brought to dryness by the above-described processes for the ethyl acetate extract, the treatment being repeated with methanol, resulting in new lots of maslinic acid, until a yield of some 0.2% is achieved at this process stage. The materials solubilised in methanol (some 23 kg) are all brought to dryness by combining the processes described for the ethyl acetate extract, and are then treated with 75 liters of boiling water, separating the undissolved material from the aqueous solution by centrifugation. A further hot-treatment is later carried out with the same water volume containing 5% sodium bicarbonate, likewise separating the bicarbonate aqueous solution from the residual solid. The insoluble part is then treated with the same volume of water containing 5% sodium hydroxide. The aqueous phase is separated from a brown-coloured solid material primarily comprising sodium maslinic acid salts which constitute between 0.2 and 0.5% by weight with respect to the original dry oil-foot refuse, further depending on the maslinic yield obtained in the previous phase. The subsequent hot-treatment of this previously milled solid with acidified water with hydrochloric acid results in the free acid, which is separated by centrifugation and undergoes bleaching with activated carbon as described hereinbefore. The two phases for obtaining maslinic acid thus yield some 0.5% acid with a richness in excess of 85%, although the yields, as with oleanolic acid, are to a certain extent dependent on the olive variety, their ripeness, the "history" of the oil-foot refuse and very much so on the weight ratio between the materials (pulp and stone) altogether forming the original oil-foot refuse.

I claim:

1. A process for obtaining 3-betadihydroxy-28-carboxyoleanene (oleanolic) acid, 2-alpha,3betadihidroxy-28-carboxyoleanene (maslinic) acid and by-products of at least one raw material from the residues of milled whole olives or parts thereof, from the oil cakes produced in oil-mill expellers, from the refuse from three-phase expellers and from the oil-foot refuse taken from the extraction of oil from olives in the manner known as the "two-phase" system, said process comprising:

separately isolating said acids comprising, (a) adding an essentially non-polar solvent to the raw material for a first solvent extraction;

(b) adding a second solvent more polar than said first solvent to the raw material product of step (a) for a second solvent extraction; and (c) adding a third solvent more polar than said second solvent to the raw material product of step (b) for third solvent extraction;

whereby the extracted acids are in excess of 80% purity.

2. The process of claim 1 wherein said first solvent is hexane.

3. The process of claim 1, wherein said second solvent is ethyl acetate.

4. The process of claim 1, wherein said third solvent is methanol.

5. The process of claim 1, wherein said first solvent is hexane, wherein said second solvent is ethyl acetate, wherein said third solvent is methanol.

6. The process of claim 1, further comprising refluxing the methane.

7. The process of claim 1, further comprising chemically or mechanically concentrating the extracted acids.

8. The process of claim 1, further comprising heating one or more of said solvents.

9. The process of claim 1, further comprising extracting the raw materials with liquified gases under super-critical conditions.

10. The process of claim 1, further comprising adding acidic material to the extracted maslinic acid or oleanolic acid.

* * * * *